(12) United States Patent
Matsunaga et al.

(10) Patent No.: US 9,090,886 B2
(45) Date of Patent: Jul. 28, 2015

(54) BETA-AMYLASE, GENE CODING THEREFOR AND MANUFACTURING METHOD THEREOF

(71) Applicant: Amano Enzyme Inc., Nagoya-shi (JP)

(72) Inventors: Akiko Matsunaga, Kakamigahara (JP); Hitoshi Amano, Kakamigahara (JP); Shotaro Yamaguchi, Kakamigahara (JP)

(73) Assignee: Amano Enzyme Inc., Nagoya-shi (JP)

( * ) Notice: Subject to any disclaimer, the term of this patent is extended or adjusted under 35 U.S.C. 154(b) by 115 days.

(21) Appl. No.: 13/919,248

(22) Filed: Jun. 17, 2013

(65) Prior Publication Data

US 2013/0273632 A1    Oct. 17, 2013

Related U.S. Application Data

(62) Division of application No. 12/991,465, filed as application No. PCT/JP2009/001807 on Apr. 21, 2009, now Pat. No. 8,486,682.

(30) Foreign Application Priority Data

May 8, 2008    (JP) .................................. 2008-122278

(51) Int. Cl.
| | |
|---|---|
| *C12N 9/26* | (2006.01) |
| *C12N 1/20* | (2006.01) |
| *C12N 15/00* | (2006.01) |
| *A21D 8/04* | (2006.01) |
| *C12N 9/28* | (2006.01) |
| *C12P 19/22* | (2006.01) |
| *C12R 1/07* | (2006.01) |

(52) U.S. Cl.
CPC .............. *C12N 9/2425* (2013.01); *A21D 8/042* (2013.01); *C12N 9/2417* (2013.01); *C12P 19/22* (2013.01); *C12R 1/07* (2013.01); *C12Y 302/01002* (2013.01)

(58) Field of Classification Search
CPC .................................................. C12N 9/2425
USPC ........................................................ 435/201
See application file for complete search history.

(56) References Cited

U.S. PATENT DOCUMENTS

2012/0121760 A1    5/2012    Matsunaga et al.

FOREIGN PATENT DOCUMENTS

| CN | 101153276 A | 4/2008 |
|---|---|---|
| JP | 60-002185 A | 1/1985 |
| WO | WO-2009/111513 A1 | 9/2009 |

OTHER PUBLICATIONS

Zhao, J. et al., "Isolation and identification of an alkaliphilic *Bacillus flexus* XJU-3 and analysis of its alkaline amylase," PubMed, Aug. 30, 2008, PMID:18720839 Wei Sheng Wu Xue Bao. Jun. 4, 2008;48(6):750-6 (2 pages).
Lee, J.S.et al., "Cloning, expression, and carbon catabolite repression of the *bamM* gene encoding beta-amylase of *Bacillus megaterium* DSM319," Appl. Microbiol. Biotechnol., 2001, vol. 56, No. 1-2, pp. 205-211 and information page.
"Beta-amylase (EC 3.2.1.2.).", Uniprot, Apr. 29, 2008, Accession:A5JUT4. (2 sheets).
"Kogyoyo Toshitsu Kouso (Handbook of Industrial Sugar Enzyme)," KODANSHA-Scientific 1999, pp. 25-27.
H. Outtrup et al., "Properties and Application of a Thermostable Maltogenic Amylase Produced by a Strain of *Bacillus* Modified by Recombinant-DNA Techniques," Starch 36, 1984, pp. 405-411.
International Search Report dated Jun. 9, 2009, issued for PCT/JP2009/001807.
J.-S. Lee et al., "Cloning, expression, and carbon catabolite repression of the *bamM* gene encoding beta-amylase of *Bacillus megaterium* DSM319," Applied Microbiology and Biotechnology, vol. 56, 2001, pp. 205-211.
Supplemental Search Report dated Apr. 26, 2012, issued for the corresponding European patent application No. 09742596.1.
European Search Report from EP Application No. 09742596.1-1410, dated Jan. 8, 2014.

*Primary Examiner* — Tekchand Saidha
(74) *Attorney, Agent, or Firm* — Locke Lord LLP

(57) ABSTRACT

To provide novel β-amylase derived from a microorganism and a gene thereof. β-amylase derived from *Bacillus flexus* is provided.

4 Claims, 6 Drawing Sheets

BETA-AMYLASE, GENE CODING THEREFOR AND MANUFACTURING METHOD THEREOF

This application is a divisional application of U.S. application Ser. No. 12/991,465, filed Nov. 8, 2010 which claims the right of priority under 35 U.S.C. §119 based on Japanese Patent Application No. 2008-122278 filed May 8, 2008.

TECHNICAL FIELD

The present invention relates to a novel β-amylase. More particularly, the present invention relates to a β-amylase derived from a microorganism, a gene thereof, and a manufacturing method thereof.

BACKGROUND ART

Conventionally, β-amylase of plant origin, for example, β-amylase from soybeans, wheat, barley, malt, a sweet potato, and a potato has been known. Among them, β-amylase extracted and purified from grains such as soybeans, wheat, barley, and malt is industrially widely used for manufacturing, for example, maltose-containing syrup used in sugar production, bakery, and brewing industries. Among the β-amylase of plant origin, β-amylase derived from soybeans has a high enzymatic activity and also an excellent thermostability.

By the way, in recent years, due to the increase in demand for bioethanol, the price of corn has risen. Consequently, planting has been shifted from soybeans or wheat to corn. Therefore, soybeans, wheat, barley, and the like, are in short supply, and the prices thereof are rising. Under such circumstances, it is difficult to secure raw materials of β-amylase.

β-amylase is an enzyme that acts on polysaccharides such as starch and glycogen, which have the α-1,4 linkage of glucose as a main chain, and breaks down them in a maltose unit from the non-reducing end. β-amylase has traditionally been known to be found in higher plants such as soybeans and wheat. Since 1972 when it was reported that an enzyme exhibiting the action mechanism the same as that of higher plant β-amylase was present also in microorganisms, a large number of microorganisms have been found as β-amylase-producing microorganisms (Non-patent Document 1).

To date, *Bacillus* sp. such as *Bacillus cereus*, *Bacillus polymyxa*, *Bacillus circulans*, *Bacillus megaterium*, and *Bacillus stearothermophilus*, *Streptomyces* sp., *Pseudomonas* sp., and the like, have been reported as the β-amylase-producing microorganisms. However, most of them have low productivity, and few of them have been practically used.

On the other hand, amylase produced by filamentous fungi such as *Aspergillus* sp., breaks down amylose and amylopectin by the end type. Therefore, when the amylase of this type is used, glucose, maltotriose, and other oligosaccharides, in addition to maltose, are produced. Furthermore, the amylase of this type has a low thermostability and is less practical for production of maltose.

*Bacillus stearothermophilus* produces a maltose-producing enzyme having a high thermostability (see, Patent Document 1 and Non-Patent Document 2). This enzyme produces maltose by the exo type from the non-reducing end of starch, but maltose produced is c type. Furthermore, this enzyme does not hydrolyze strictly in a maltose unit as in β-amylase of plant origin. That is to say, it is reported that, in the initial time of reaction, in addition to maltotetraose (G4), maltotriose (G3) and maltose (G2), a small amount of maltopentaose (G5) and maltohexaose (G6) are also produced, and that this enzyme breaks down Shardinger dextrin into maltose and glucose, and breaks down maltotriose into maltose and glucose. As a result, in the starch decomposed product by this enzyme, 6 to 8% glucose is contained. Therefore, this enzyme is not suitable for manufacturing highly purified maltose syrups.

CITATION LIST

Patent Documents

[Patent Document 1] Japanese Patent Application Unexamined Publication No. S60-2185

Non-Patent Documents

[Non-Patent Document 1] "Handbook of Industrial Sugar Enzyme," Kodansha Scientific, 1999
[Non-Patent Document 2] H. Outtrup and B. E. Norman, Starch, Vol. 36, pages 405 to 411

DISCLOSURE OF THE INVENTION

Problems to be Solved by the Invention

As mentioned above, it is difficult to secure stable supply of β-amylase of plant origin that is a mainstream at the present time. Furthermore, the amount of enzyme obtained from plants is preliminarily determined, and the production amount is limited. On the other hand, few of β-amylase derived from microorganisms have been practically used because the productivity is low or mass production is difficult.

Means to Solve the Problem

In view of the above-mentioned problems, the present inventors have keenly investigated, and, as a result, have found that *Bacillus flexus* of *Bacillus subtilis* produces β-amylase having a thermostability comparable to that of β-amylase derived from soybeans. Furthermore, the present inventors have succeeded in isolating and purifying the β-amylase, and determining enzymological properties. Furthermore, the present inventors have succeeded in determining a base sequence of a gene encoding the β-amylase. In addition, they have confirmed that it is possible to manufacture β-amylase by using a transformant into which a vector containing the gene has been introduced.

The present invention has been completed based on the above-mentioned results and includes the followings.

[1] A β-amylase derived from *Bacillus flexus*.

[2] A β-amylase having the following enzymological properties:

(1) action: acting on the α-1,4 glucoside linkage of polysaccharides and oligosaccharides to liberate maltose;

(2) substrate specificity: acting well on starch, amylose, amylopectin, glycogen, maltotetraose, maltopentaose, maltohexaose, and maltoheptaose, but not acting on pullulan, dextran, cyclodextrin, and maltotriose;

(3) optimum temperature: about 55° C.;

(4) optimum pH: about 8.0;

(5) thermostability: stable at 55° C. or lower (pH 5.0, 10 minutes);

(6) pH stability: stable at pH 4 to 9 (30° C., three hours); and (7) molecular weight: about 60,000 (SDS-PAGE).

[3] A β-amylase having an amino acid sequence set forth in SEQ ID NO: 7, or an amino acid sequence equivalent to the amino acid sequence.

[4] The β-amylase described in [3], wherein the equivalent amino acid sequence is an amino acid sequence having about 90% or more identity to the amino acid sequence set forth in SEQ ID NO: 7.

[5] An enzyme preparation including β-amylase described in any one of [1] to [4] as an active ingredient.

[6] A β-amylase gene including DNA selected from the group consisting of the following (A) to (C):

(A) DNA encoding an amino acid sequence set forth in SEQ ID NO: 7;

(B) DNA having a base sequence set forth in SEQ ID NO: 6; and (C) DNA having a base sequence equivalent to the base sequence set forth in SEQ ID NO: 6, and having a β-amylase activity.

[7] A recombinant vector containing a β-amylase gene described in [6].

[8] A transformant into which a β-amylase gene described in [6] is introduced.

[9] A manufacturing method of β-amylase, the method including the following steps (1) and (2) or steps (i) and (ii):

(1) culturing *Bacillus flexus* having an ability of producing β-amylase:

(2) collecting β-amylase from a culture solution and/or a cell body after culturing;

(i) culturing a transformant described in [8] under the conditions in which a protein encoded by the gene is produced; and (ii) collecting the produced protein.

[10] The manufacturing method described in [9], wherein *Bacillus flexus* is a strain specified by the accession number NITE BP-548.

[11] A *Bacillus flexus* strain specified by the accession number NITE BP-548.

[12] A production method of maltose, the method including allowing β-amylase derived from *Bacillus flexus* to act on polysaccharide or oligosaccharide having α-1,4 linkage of glucose as a main chain.

[13] The production method described in [12], wherein the β-amylase is a β-amylase described in any one of [2] to [4].

DESCRIPTION OF EMBODIMENT

Terms

Figure 1:
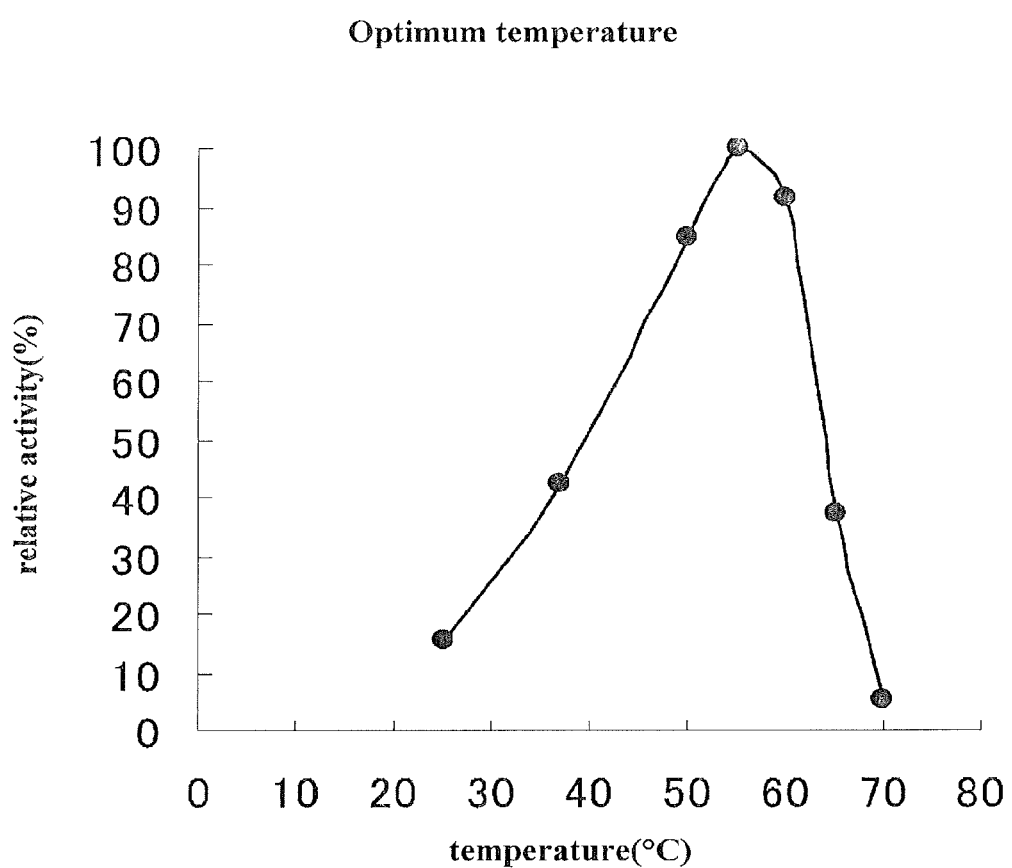
FIG. 1 is a graph showing an optimum temperature of β-amylase derived from *Bacillus flexus*.

The term "DNA encoding protein" in the present invention denotes DNA from which the protein is obtained when it is expressed, that is, DNA having a base sequence corresponding to an amino acid sequence of the protein. Therefore, the codon degeneracy is also taken into consideration.

In the present specification, the term "isolated" and "purified" are used interchangeably. The term "isolated" used with respect to the enzyme of the present invention (β-amylase), which is derived from a natural material, denotes a state in which components other than the enzyme are not substantially contained (in particular, contaminated protein is not substantially contained) in the natural material. Specifically, in the isolated enzyme of the present invention, the content of the contaminant protein is, for example, less than about 20%, preferably less than about 10%, further preferably less than about 5%, and yet further preferably less than about 1% with respect to the total amount on the weight basis. On the other hand, the term "isolated" when the enzyme of the present invention is prepared by genetically engineering technique denotes a state in which other components derived from a host cell to be used, a culture solution, and the like, are not substantially contained. Specifically, for example, in the isolated enzyme of the present invention, the content of the contaminant components is less than about 20%, preferably less than about 10%, further preferably less than about 5%, and yet further preferably less than about 1% with respect to the total amount on the weight basis. Unless otherwise specified, when merely the term "β-amylase" is used in this specification, it signifies the "β-amylase in an isolated state." The same is true to the term "the present enzyme" used instead of β-amylase.

The term "isolated" used with respect to DNA denotes typically that DNA is separated from other nucleic acid coexisting in nature when the DNA originally exists in nature. However, some of the other nucleic acid components such as a neighboring nucleic acid sequence in nature (for example, a sequence of a promoter region, a terminator sequence, or the like) may be included. For example, in the "isolated" state of the genome DNA, the isolated DNA preferably does not substantially include other DNA components coexisting in nature. On the other hand, in the "isolated" state of DNA prepared by a genetic engineering technique, for example, a cDNA molecule, and the like, preferably, the DNA does not substantially include cell components, a culture solution, or the like. Similarly, in the "isolated" state in the case of DNA prepared by chemical synthesis, the DNA does not include a precursor (a raw material) or chemical materials used in synthesis, for example, dNTP. Unless otherwise specified, when merely the term "DNA" is used in this specification, it signifies the "DNA in an isolated state."

(β-amylase and Producing Microorganism Thereof)

A first aspect of the present invention provides β-amylase (hereinafter, also referred to as "the present enzyme") and the producing microorganism thereof. As shown in the below-mentioned Example, the present inventors have keenly investigated, and, as a result, have found that *Bacillus flexus* produces thermostable β-amylase. Furthermore, the present inventors have succeeded in isolation and purification, and also succeeded in determination of its enzymological property.

(1) Action

The present enzyme is β-amylase, and it acts on the α-1,4 glucoside linkage in polysaccharides and oligosaccharides to liberate maltose. The present enzyme hardly liberates glucose.

(2) Substrate Specificity

The present enzyme is excellent in the substrate specificity and well acts on starch, amylose, amylopectin, glycogen, maltotetraose, maltopentaose, maltohexaose, and maltheptaose. On the contrary, the present enzyme does not act on pullulan, dextran, cyclodextrin, and maltotriose.

When the present enzyme has a relative activity of 50% or more with respect to the basic activity (100%) that is a value when a soluble starch is used as a substrate, the substrate is determined to be a "substrate on which an enzyme acts on well." Similarly, when the relative activity is less than 10%, the substrate is determined to be a "substrate on which the enzyme does not act." The enzyme does not substantially act on maltotriose and cyclodextrin (α, β, or γ).

Note here that the reactivity and the substrate specificity of the present enzyme can be measured and evaluated by the method shown in the below-mentioned Examples (see, column of a measurement method of the β-amylase activity).

(3) Optimum Temperature

The optimum temperature of the present enzyme is about 55° C. The present enzyme shows high activity at a temperature in the range from about 50° C. to about 60° C. The optimum temperature is a value calculated by the below-mentioned measurement method of β-amylase activity (0.1 M phosphate-HCl buffer solution (pH 5.0)).

(4) Optimum pH

The optimum pH of the present enzyme is about 8.0. The present enzyme shows high activity in the range from pH about 6.0 to about 9.0. The optimum pH is determined, for example, based on the results of the measurement in a citric acid buffer with respect to pH region of pH 2 to 4, and based on the results of the measurement in a Britton-Robinson buffer with respect to pH region of pH 4 to 11.

(5) Thermostability

The present enzyme shows an excellent thermostability that is comparable to that of β-amylase derived from soybeans. The present enzyme maintains 90% or more of the activity in 0.1M acetic acid-hydrochloric acid buffer solution (pH 5.0) containing 10 mM calcium acetate at 55° C. for 10 minutes.

(6) pH Stability

The enzyme shows stable activity in such a wide pH range as pH 4 to 9. That is to say, when pH of an enzyme solution subjected to treatment is within the range, the enzyme shows 70% or more activity with respect to the maximum activity after treatment at 30° C. for three hours. The optimum pH is determined, for example, based on the results of the measurement in a citric acid buffer for the pH region of pH 2 to 4, and based on the results of the measurement in a Britton-Robinson buffer for the pH region of pH 4 to 11.

(7) Molecular Weight

The molecular weight of the enzyme is about 60,000 (by SDS-PAGE).

Preferably, the present enzyme is β-amylase derived from *Bacillus flexus*. Herein, the "β-amylase derived from *Bacillus flexus*" denotes β-amylase produced by microorganisms classified in *Bacillus flexus* (which may be wild-type strain and mutant strain), or β-amylase produced by using a β-amylase gene of *Bacillus flexus* (which may be wild-type strain and mutant strain) obtained by a genetic engineering technique. Therefore, the "β-amylase derived from *Bacillus flexus*" includes a recombinant produced by using a host microorganism into which a β-amylase gene (or a gene obtained by modifying the gene) obtained from *Bacillus flexus* has been introduced.

*Bacillus flexus* from which the present enzyme is derived is represented by a producing microorganism of the present enzyme for easy description. Examples of the producing microorganism of the present enzyme may include *Bacillus flexus* DSM1316 (DSMZ, Germany), DSM1320 (DSMZ, Germany), DSM1667 (DSMZ, Germany), and APC9451. The APC9451 strain is deposited with the predetermined depositary as mentioned below, and easily available.

Depositary institution: Department of Biotechnology, National Institute of Technology and Evaluation (NITE), Patent Microorganisms Depositary Center (2-5-8, Kazusa Kamatari, Kisarazu-shi, Chiba, 292-0818, Japan)

Deposited date (accepted date): Apr. 9, 2008

Accession number: NITE BP-548

As mentioned above, the details of the property of the present enzyme that has been successfully obtained has been clarified. As a result, it has been revealed that the present enzyme is excellent in thermostability and excellent in substrate specificity. Therefore, the present enzyme is useful for food processing and saccharification.

The present inventors have further investigated and, as a result, have determined an amino acid sequence (SEQ ID NO: 7) of β-amylase produced by *Bacillus flexus*. Thus, one embodiment of the present invention is characterized in that the present enzyme consists of a protein having an amino acid sequence set forth in SEQ ID NO: 7. Herein, in general, when a part of the amino acid sequence of a certain protein is modified, the modified protein may sometimes have a function the same as that of the protein before modification. That is to say, the modification of the amino acid sequence does not have a substantial effect on the function of the protein, so that the function of the protein may be maintained before and after the modification. As another embodiment, the present invention provides a protein having an amino acid sequence equivalent to the amino acid sequence set forth in SEQ ID NO: 7 and having the β-amylase activity (hereinafter, which is referred to as "equivalent protein"). The "equivalent amino acid sequence" herein denotes an amino acid sequence that is partly different from the amino acid sequence set forth in SEQ ID NO: 7 but this difference does not have a substantial effect on the function (herein, the β-amylase activity) of the protein. The term "having a β-amylase activity" denotes having an activity of acting on polysaccharides or oligosaccharides of glucose such as starch and glycogen, which has the α-1,4 linkage as a main chain, thus breaking down a maltose unit from the non-reducing end. However, the degree of the activity is not particularly limited as long as the function of β-amylase can be exhibited. However, it is preferable that the activity is equal to or higher than that of the protein having the amino acid sequence set forth in SEQ ID NO: 7.

The "partial difference in the amino acid sequence" typically denotes that mutation (change) occurs in an amino acid sequence due to deletion or substitution of one to several amino acids constituting the amino acid sequence, or addition or insertion of one to several amino acids, or the combination thereof. Herein, the difference in the amino acid sequence is permitted as long as the β-amylase activity is maintained (more or less change in the activity is permitted). As long as this condition is satisfied, the position in which a difference in the amino acid sequence occurs is not particularly limited and the difference may occur in a plurality of positions. The plurality herein signifies a numerical value corresponding to less than about 30%, preferably less than about 20%, further preferably less than about 10%, still further preferably less than about 5%, and most preferably less than about 1% with respect to the total amino acid. That is to say, the equivalent protein has, for example, about 70% or more, preferably about 80% or more, further preferably about 90% or more, still further preferably about 95% or more and most preferably about 99% or more identity to the amino acid sequence set forth in SEQ ID NO: 7.

Preferably, an equivalent protein is obtained by allowing conservative amino acid substitution to be generated in an amino acid residue that is not essential to the β-amylase activity. Herein, "conservative amino acid substitution" denotes substitution of an amino acid residue to an amino acid residue having a side chain of the same property. The amino acid residue is classified into some families according to its side chain, for example, the basic side chain (for example, lysin, arginine, and histidine), the acid side chain (for example, asparatic acid, and glutamic acid), the uncharged polar side chain (for example, glycine, asparagine, glutamine, serine, threonine, tyrosine, and cysteine), the nonpolar side chain (for example, alanine, valine, leucine, isoleucine, proline, phenyl alanine, methionine, and tryptophane), β branched side chain (for example, threonine, valine, and isoleucine), and the aromatic side chain (for example, tyrosine, phenyl alanine, tryptophane, and histidine). The conservative amino acid substitution is carried out between the amino acid residues in the same family.

The "equivalent protein" may have an additional property. Examples of such a property include a property that stability is more excellent than the protein including the amino acid sequence set forth in SEQ ID NO: 7, a property that function that is different only at low temperature and/or high temperature is exhibited, and a property that an optimum pH is different.

The identity (%) between two amino acid sequences or two nucleic acids (hereinafter, referred to as "two sequences" as a term including the both) can be determined by the following procedure. Firstly, two sequences are aligned for optimum comparison of the two sequences (for example, a gap may be introduced into the first sequence so as to optimize the alignment with respect to the second sequence). When a molecule (amino acid residue or nucleotide) at a specific position in the first sequence and a molecule in the corresponding position in the second sequence are the same as each other, the molecules in the positions are defined as being identical. The identity between two sequences is a function of the number of identical positions shared by the two sequences (i.e., identity (%)=number of identical positions/total number of positions×100). Preferably, the number and size of the gaps, which are required to optimize the alignment of the two sequences, are taken into consideration.

The comparison and determination of the identity between two sequences can be carried out by using a mathematical algorithm. A specific example of the mathematical algorithm that can be used for comparing the sequences includes an algorithm described in Karlin and Altschul (1990) Proc. Natl. Acad. Sci. USA 87:2264-68 and modified by Karlin and Altschul (1993) Proc. Natl. Acad. Sci. USA 90:5873-77. However, the algorithm is not necessarily limited to this. Such an algorithm is incorporated in NBLAST program and XBLAST program (version 2.0) described in Altschul et al. (1990) J. Mol. Biol. 215: 403-10. In order to obtain a nucleotide sequence equivalent to the nucleic acid molecule of the present invention, for example, BLAST nucleotide search with score=100 and word length=12 may be carried out by the NBLAST program. In order to obtain an amino acid sequence equivalent to the polypeptide molecule of the present invention, for example, BLAST polypeptide search with score=50 and word length=3 may be carried out by the XBLAST program. In order to obtain gapped alignments for comparison, Gapped BLAST described in Altschul et al., (1997) Amino Acids Research 25(17): 3389-3402 can be utilized. In using BLAST and Gapped BLAST, the default parameters of the corresponding programs (e.g., XBLAST and NBLAST) can be used. In detail, see http://www.ncbi.nlm.nih.gov. Another example of the mathematical algorithm that can be used for comparing sequences includes an algorithm described in Meyers and Miller (1988) Comput. Appl. Biosci. 4: 11-17. Such programs are incorporated into the ALIGN program that can be used for, for example, GENESTREAM network server (IGH Montpellier, France) or ISREC server. When the ALIGN program is used for comparison of the amino acid sequences, for example, PAM120 weight residue table can be used in which a gap length penalty is 12 and a gap penalty is 4.

The identity between two amino acid sequences can be determined by using the GAP program in the GCG software package, using Blossom 62 matrix or PAM250 matrix with the gap weight of 12, 10, 8, 6, or 4, and the gap length weight of 2, 3, or 4. Furthermore, the homology between two nucleic acid sequences can be determined using the GAP program in the GCG software package (available at http://www.gcg.com) with the gap weight of 50 and the gap length weight of 3.

The present enzyme may be a part of a larger protein (for example, fusion protein). Examples of a sequence to be added in the fusion protein may include a sequence useful for purification, for example, a sequence of a multi histidine residue, and an additional sequence for securing the safety for producing a recombinant, and the like.

The present enzyme having the above-mentioned amino acid sequence can be prepared easily by a genetic engineering technique. For example, the present enzyme can be prepared by transforming an appropriate host cell (for example, *Escherichia coli*) by DNA encoding the present enzyme, and by collecting proteins expressed in the transformant. The collected proteins are appropriately purified according to the purposes. In the case where the present enzyme is prepared as a recombinant protein, various modifications can be carried out. For example, DNA encoding the present enzyme and other appropriate DNA are inserted into the same vector and the vector is used for producing a recombinant protein. Then, the enzyme consisting of a recombinant protein to which arbitrary peptide or protein is linked can be obtained. Furthermore, modification may be carried out so as to cause addition of sugar chain and/or lipid or processing of N-terminal or C-terminal. The above-mentioned modification permits extraction of a recombinant protein, simplification of purification, addition of biological functions, or the like.

(DNA Encoding β-amylase)

A second aspect of the present invention provides a gene encoding the present enzyme, that is, a novel β-amylase gene. In one embodiment, the gene of the present invention includes DNA encoding the amino acid sequence set forth in SEQ ID NO: 7. A specific example of this embodiment is a DNA consisting of the base sequence set forth in SEQ ID NO: 6.

In general, when a part of DNA encoding a certain protein is modified, a protein encoded by the modified DNA may sometimes have the equal function to that of a protein encoded by the DNA before modification. That is to say, the modification of the DNA sequence does not have a substantial effect on the function of the encoded protein, so that the function of the encoded protein may be maintained before and after the modification. Thus, as another embodiment, the present invention provides DNA encoding a protein having a base sequence equivalent to the base sequence set forth in SEQ ID NO: 6 and having the β-amylase activity (hereinafter, which is also referred to as "equivalent DNA"). The "equivalent base sequence" herein denotes a base sequence which is partly different from the base sequence set forth in SEQ ID NO: 6 but in which the function (herein, β-amylase activity) of the protein encoded by the sequence is not substantially affected by the difference.

A specific example of the equivalent DNA includes DNA that hybridizes to the complementary base sequence of the base sequence of SEQ ID NO: 6 under stringent conditions. Herein, the "stringent conditions" are referred to as conditions in which a so-called specific hybrid is formed but a nonspecific hybrid is not formed. Such stringent conditions are known to persons skilled in the art. Such stringent conditions can be set with reference to, for example, Molecular Cloning (Third Edition, Cold Spring Harbor Laboratory Press, New York) and Current protocols in molecular biology (edited by Frederick M. Ausubel et al., 1987). An example of the stringent conditions can include a condition in which a hybridization solution (50% formamide, 10×SSC (0.15 M NaCl, 15 mM sodium citrate, pH 7.0), 5×Denhardt solution, 1% SDS, 10% dextran sulfate, 10 kg/ml denatured salmon sperm DNA, and 50 mM phosphate buffer (pH 7.5)) is used and incubated at about 42° C. to about 50° C., thereafter, washed with 0.1×SSC and 0.1% SDS at about 65° C. to about 70° C. Further preferable stringent conditions can include, for example, a condition in which a hybridization solution 50% formamide, 5×SSC (0.15 M NaCl, 15 mM sodium citrate, pH 7.0), 1×Denhardt solution, 1% SDS, 10% dextran sulfate, 10 μg/ml denatured salmon sperm DNA, and 50 mM phosphate buffer (pH 7.5)) is used.

Another specific example of the equivalent DNA can include DNA encoding a protein having a base sequence which includes substitution, deletion, insertion, addition or inversion in one or a plurality of bases when the base sequence of SEQ ID NO: 6 is a reference base sequence, and which has a β-amylase activity. The substitution, deletion, or the like, of the base may occur in a plurality of sites. The "plurality" herein denotes, for example, 2 to 40 bases, preferably 2 to 20 bases, and more preferably 2 to 10 bases, although it depends upon the positions or types of the amino acid residue in the three-dimensional structure of the protein encoded by the DNA. The above-mentioned equivalent DNA can be obtained by modifying DNA having the base sequence shown in SEQ ID NO: 6 so as to include substitution, deletion, insertion, addition and/or inversion of base by using treatment with a restriction enzyme; treatment with exonuclease, DNA ligase, etc.; introduction of mutation by a site-directed mutagenesis (Molecular Cloning, Third Edition, Chapter 13, Cold Spring Harbor Laboratory Press, New York) and random mutagenesis (Molecular Cloning, Third Edition, Chapter 13, Cold Spring Harbor Laboratory Press, New York), and the like. Furthermore, the equivalent DNA can be also obtained by other methods such as irradiation with ultra-violet ray.

A further example of the equivalent DNA can include DNA having difference in base as mentioned above due to polymorphism represented by SNP (single nucleotide polymorphism).

The gene of the present invention can be prepared in an isolated state by using a standard genetic engineering technique, a molecular biological technique, a biochemical technique, and the like, with reference to sequence information disclosed in the present specification or attached sequence list. Specifically, the gene of the present invention can be prepared by appropriately using oligonucleotide probe/primer capable of specifically hybridizing to the gene of the present invention from an appropriate genome DNA library or a cDNA library of *Bacillus flexus*, or cell body extract of *Bacillus flexus*. An oligonucleotide probe/primer can be easily synthesized by using, for example, a commercially available automated DNA synthesizer. As to a production method of libraries used for preparing the gene of the present invention, see, for example, Molecular Cloning, Third Edition, Cold Spring Harbor Laboratory Press, New York.

For example, a gene having the base sequence set forth in SEQ ID NO: 6 can be isolated by using a hybridization method using all or a part of the base sequence or its complimentary sequence as a probe. Furthermore, amplification and isolation can be carried out by using a nucleic acid amplification reaction (for example, PCR) using a synthesized oligonucleotide primer designed to specifically hybridize to a part of the base sequence. Furthermore, it is possible to obtain a target gene by chemical synthesis based on the information of the amino acid sequence set forth in SEQ ID NO: 7 or the base sequence set forth in SEQ ID NO: 6 (see, reference document: Gene, 60(1), 115-127 (1987)).

Hereinafter, a specific example of the method of obtaining the gene of the present invention is described. Firstly, the present enzyme (β-amylase) is isolated and purified from *Bacillus flexus*, and information about the partial amino acid sequence is obtained. As a method for determining the partial amino acid sequence thereof, for example, purified β-amylase is directly subjected to amino acid sequence analysis [protein-sequencer 476A, Applied Biosystems] by Edman Degradation [Journal of biological chemistry, vol. 256, pages 7990-7997 (1981)] according to a routine method. It is effective that limited hydrolysis is carried out by allowing protein hydrolase to act, the obtained peptide fragment is separated and purified, and the thus obtained purified peptide fragment is subjected to the amino acid sequence analysis.

Based on the information of thus obtained partial amino acid sequence, a β-amylase gene is cloned. Cloning can be carried out by using, for example, a hybridization method or a PCR method. When the hybridization method is used, for example, a method described in Molecular Cloning (Third Edition, Cold Spring Harbor Laboratory Press, New York) can be used.

When the PCR method is used, the following method can be used. Firstly, PCR reaction is carried out by using a synthesized oligonucleotide primer designed based on the information of the partial amino acid sequence using a genome DNA of a microorganism producing β-amylase as a template, and thus a target gene fragment is obtained. The PCR method is carried out according to the method described in PCR Technology, edited by Erlich, H A, Stocktonpress, 1989]. Furthermore, when a base sequence is determined by a method usually used in the amplification DNA fragment, for example, a dideoxy chain terminator method, a sequence corresponding to the partial amino acid sequence of β-amylase other than the sequence of the synthesized oligonucleotide primer is found in the determined sequence, and a part of the β-amylase gene can be obtained. When a hybridization method and the like is further carried out by using the obtained gene fragment as a probe, a gene encoding the full length of the β-amylase can be cloned.

In the below mentioned Examples, a sequence of a gene encoding β-amylase produced by *Bacillus flexus* is determined by using the PCR method. The complete base sequence of a gene encoding β-amylase produced by *Bacillus flexus* is shown in SEQ ID NO: 6. Furthermore, the amino acid sequence encoded by the base sequence is determined (SEQ ID NO: 7). In addition to the base sequence shown in SEQ ID NO: 6, a plurality of the base sequences corresponding to the amino acid sequence set forth in SEQ ID NO: 7 are present.

All or a part of the β-amylase gene (SEQ ID NO: 6) whose complete base sequence has been clarified is used as a probe of hybridization, and thereby DNA having high homology with respect to the β-amylase gene of SEQ ID NO: 6 can be selected from a genome DNA library or a cDNA library of microorganisms producing other β-amylase.

Similarly, a primer for PCR can be designed. By carrying out PCR reaction using this primer, a gene fragment having high homology with respect to the above-mentioned β-amylase gene can be detected and, furthermore, a complete gene thereof can be obtained.

Protein of the obtained gene is manufactured, and its β-amylase activity is measured. Thereby, it is possible to confirm whether or not the obtained gene is a gene encoding a protein having the β-amylase activity. Furthermore, by comparing the base sequence (or the amino acid sequence encoded thereby) of the obtained gene with the base sequence (or the amino acid sequence encoded thereby) of the above-mentioned β-amylase gene, the gene structure or the homology may be examined, thereby determining whether or not the gene encodes protein having the β-amylase activity.

Since the primary structure and the gene structure are clarified, modified β-amylase (a gene subjected to at least one of deletion, addition, insertion, and substitution of one or a plurality of amino acid residues) can be obtained by introduction of random mutation or site-specific mutation. This makes it possible to obtain a gene encoding β-amylase that has a β-amylase activity but has different optimum temperature, thermostability, optimum pH, stable pH, substrate specificity, and the like. Furthermore, it becomes possible to manufacture modified β-amylase by genetic engineering.

Herein, a scheme for introducing mutation is carried out with consideration of, for example, a characteristic sequence of a gene sequence. The consideration of a characteristic sequence can be made by considering, for example, the prediction of the three-dimensional structure of the protein, and homology to existing proteins.

Examples of the method for introducing random mutation include: a method, as method of chemically treating DNA, which causes transition mutation in which sodium hydrogensulfite is allowed to act and cytosine base is converted into uracil base [Proc. Natl. Acad. Sci. U.S.A., 79, 1408-1412 (1982)]; a method, as a biochemical method, which causes base substitution during the process of synthesizing the double strand in the presence of [α-S]dNTP [Gene, vol 64, pages 313-319 (1988)]; a method, as a method of using PCR, which carries out PCR in a reaction system with manganese added, thereby lowering fidelity of incorporation of nucleotides [Anal. Biochem., 224, 347-353 (1995)], and the like.

Examples of the method for introducing site-specific mutation include a method using amber mutation [gapped duplex method; Nucleic Acids Res., Vol. 12, No. 24, 9441-9456 (1984)]; a method using a recognition site of the restriction enzyme [Analytical Biochemistry, Vol. 200, pages 81-88 (1992), Gene, Vol. 102, pages 67-70 (1991)]; a method using mutation of dut (dUTPase) and ung (uracil-DNA glycosilase) [Kunkel method; Proc. Natl. Acad. Sci. U.S.A., 82, 488-492 (1985)]; a method using amber mutation using DNA polymerase and DNA ligase [Oligonucleotide-directed Dual Amber: ODA) method, Gene, Vol. 152, pages 271-275 (1995), Japanese Patent Application Unexamined Publication No. H7-289262]; a method using a host inducing a repair system of DNA (Japanese Patent Application Unexamined Publication No. H8-70874); a method using a protein catalyzing a DNA strand exchange reaction (Japanese Patent Application Unexamined Publication No. H8-140685); a method by PCR using two types of primers for introducing a restriction enzyme into which the recognition site is added (U.S. Pat. No. 5,512,463); a method by PCP using a double strand DNA vector having inactivated drug-resistant gene and two types of primers [Gene, Vol. 103, pages 73-77 (1991)]; a method by PCR using amber mutation [International Publication WO98/02535], and the like.

The site-specific mutation can be easily introduced by using commercially available kits. Examples of the commercially available kits include Mutan-G (register trade mark, Takara Shuzo Co., Ltd.) using the gapped duplex method, Mutan-K (register trade mark, Takara Shuzo Co., Ltd.) using the Kunkel method, Mutan-ExpressKm (register trade mark, Takara Shuzo Co., Ltd.) using the ODA method, QuikChange™ Site-Directed Mutagenesis Kit [STRATAGENE] using a primer for introducing mutation and DNA polymerase derived from *Pyrococcus furiosus*, and the like. Furthermore, as the kits using the PCR method, for example, TaKaRa LA PCR in vitro Mutagenesis Kit (Takara Shuzo Co., Ltd.), Mutan (register trade mark)—Super Express Km (Takara Shuzo Co., Ltd.), and the like.

Thus, the primary structure and the gene structure of β-amylase are provided by the present invention. As a result, it is possible to genetically manufacture proteins having a β-amylase activity with high purity at low cost.

(Recombinant Vector)

Another aspect of the present invention relates to a recombinant vector containing the gene of the present invention. The term "vector" as used in this specification is intended to refer to a nucleic acid molecule capable of transporting nucleic acid that is inserted in the vector to the inside of the target such as cells. The types or forms of vector are not particularly limited. Therefor, examples of the vector may be in a form of a plasmid vector, a cosmid vector, a phage vector, a viral vector (e.g., an adenovirus vector, an adeno-associated virus vector, a retrovirus vector, a herpes virus vector, etc.).

According to the purpose of use (cloning, protein expression), and by considering the types of host cells, an appropriate vector is selected. Specific examples of the vector include a vector using *Escherichia coli* as a host (M13 phage or the modified body thereof, λ phage or the modified body thereof, pBR322 or the modified body thereof (pB325, pAT153, pUC8, etc.) and the like), a vector using yeast as a host (pYepSec1, pMFa; pYES2, etc.), a vector using insect cells as a host (pAc, pVL, etc.), a vector using mammalian cells as a host (pCDM8, pMT2PC, etc.), and the like.

The recombinant vector of the present invention is preferably an expression vector. The term "expression vector" is a vector capable of introducing the nucleic acid inserted therein into the target cells (host cells) and being expressed in the cells. The expression vector usually includes a pronioter sequence necessary for expression of the inserted nucleic acid and an enhancer sequence for promoting the expression, and the like. An expression vector including a selection marker can be used. When such an expression vector is used, by using the selection marker, the presence or absence of the introduction of an expression vector (and the degree thereof) can be confirmed.

Insertion of the gene of the present invention into a vector, insertion of the selection marker gene (if necessary), and insertion of a promoter (if necessary), and the like, can be carried out by a standard recombination DNA technology (see, for example, Molecular Cloning, Third Edition, 1.84, Cold Spring Harbor Laboratory Press, New York, a already-known method using restriction enzyme and DNA ligase).

(Transformant)

The present invention further relates to a transformant into which the gene of the present invention is introduced. In the transformant of the preset invention, the gene of the present invention exists as an exogenous molecule. Preferably, the transformant of the present invention can be preferably prepared by transfection or transformation using the vector of the present invention mentioned above. The transfection and transformation can be carried out by, for example, a calcium phosphate coprecipitation method, electroporation (Potter, H, et al., Proc. Natl. Acad. Sci. U.S.A. 81, 7161-7165(1984)), lipofection (Felgner, P. L. et al., Proc. Natl. Acad. Sci. U.S.A. 84,7413-7417 (1984)), microinjection (Graessmann, M. & Graessmann, A., Proc. Natl. Acad. Sci. U.S.A. 73,366-370 (1976)), a method by Hanahan (Hanahan, D., J. Mol. Biol. 166, 557-580 (1983)), a lithium acetate method (Schiestl, R. H. et al., Curr. Genet. 16, 339-346 (1989)), protoplast—polyethylene glycol method (Yelton, M. M. et al., Proc. Natl. Acad. Sci. 81, 1470-1474 (1984)), and the like.

Examples of the host cell may include microorganism, animal cells, plant cells, and the like. Examples of microorganisms may include bacterial cells such as *Escherichia coli, Bacillus* sp., *Streptomyces* sp., and *Lactococcus* sp.; yeast such as *Saccharomyces* sp., *Pichia* sp., and *Kluyveromyces* sp.; filamentous fungi such as *Aspergillus* sp., *Penicillium* sp., and *Trichoderma* sp. As the animal cell, baculovirus may be used.

(Manufacturing Method of β-amylase)

A further aspect of the present invention provides a manufacturing method of β-amylase. In one embodiment of the manufacturing method of the present invention, a step of culturing *Bacillus flexus* having ability of producing the present enzyme (β-amylase) (step (1)), and a step of collecting the β-amylase from a culture solution and/or a cell body after culture (step (2)) are carried out.

Examples of *Bacillus flexus* to be used in the step (1) may include the above-mentioned *Bacillus flexus* DSM1316, DSM1320, DSM1667, APC9451, and the like. The culturing method and the culture conditions are not particularly limited as long as the target enzyme is produced. That is to say, on the condition that the present enzyme is produced, a methods and culture conditions suitable for culturing of microorganisms to be used can be set appropriately. As the culture method, any of liquid culture and solid culture may be employed, but liquid culture is preferred. The culture conditions are described taking liquid culture as an example.

Any media can be used as long as microorganisms to be used can grow. For example, a medium containing a carbon source such as glucose, sucrose, gentiobiose, soluble starch, glycerin, dextrin, syrup, and organic acids; a nitrogen source such as ammonium sulfate, ammonium carbonate, ammonium phosphate, ammonium acetate, or peptone, yeast extract, corn steep liquor, casein hydrolysate, bran, meat extract, and the like; and further, inorganic salts such as potassium salt, magnesium salt, sodium salt, phosphate salt, manganese salt, iron salt, and zinc salt, can be used. In order to promote the growth of microorganisms to be used, vitamin, amino acid, and the like may be added to the medium. The pH of the medium is adjusted to, for example, about 3 to 10, and preferably, about 7 to 8. The culturing temperature is generally about 10° C. to 50° C., and preferably about 20° C. to 37° C. The culturing is carried out for one to seven days, preferably three to four days under aerobic conditions. As a culturing method, for example, a shake culture method, and an aerobic submerged culture method with a jar fermenter can be employed.

After the culturing in the above-mentioned conditions, β-amylase is collected from the culture solution or the cell body (step (2)). When β-amylase is collected from the culture solution, the present enzyme can be obtained by separation and purification after removing insoluble matters by, for example, filtration, centrifugation of culture supernatant followed by carrying out any combinations of concentration by ultrafiltration, salting out of ammonium sulfate precipitation, dialysis, various types of chromatography such as ion-exchange resin, and the like.

On the other hand, when the present enzyme is collected from the cell body, the present enzyme can be obtained by pulverizing the cell body by pressuring treatment, ultrasonication, and the like, followed by separation and purification thereof similar to the above. Note here that the above-mentioned series of processes (pulverizing, separation, and purification of cell body) may be carried out after the cell body is collected from a culture solution by filtration, centrifugation, and the like.

Note here that confirmation of expression or confirmation of expression product can be carried out easily by using an antibody against β-amylase, but expression can be confirmed by measuring the β-amylase activity.

According to another embodiment of the present invention, β-amylase is manufactured by using the above-mentioned transformant. In the manufacturing method in this embodiment, firstly, the above-mentioned transformant is cultured in the conditions in which the protein encoded by the introduced gene is produced (step (i)). As to various vector-host systems, the culture conditions for transformant are well-known, and a person skilled in the art can set appropriate culture conditions easily. After the culturing step, a step of collecting the produced protein (i.e., β-amylase) is carried out (step (ii)). Collection and the following purification may be carried out by the same method as mentioned in the above-mentioned embodiment. The purification degree of the present enzyme is not particularly limited. Furthermore, the final form may be a liquid state or a solid state (including a powder state).

(Enzyme Preparation)

The enzyme of the present invention is provided in a form of, for example, an enzyme preparation. The enzyme preparation may contain, in addition to an active ingredient (the enzyme of the present invention), excipient, buffer agents, suspension agents, stabilizer, preservatives, antiseptics, physiologic saline, and the like. Examples of the excipient may include lactose, sorbitol, D-mannitol, sucrose, and the like. Examples of the buffer agent may include phosphate, citrate, acetate, and the like. Examples of the stabilizer may include propylene glycol, and ascorbic acid, and the like. Examples of the preservative may include phenol, benzalkonium chloride, benzyl alcohol, chlorobutanol, methyl paraben, and the like. Examples of the antiseptic may include benzalkonium chloride, parahydroxybenzoate, chlorobutanol, and the like.

(Application of β-amylase)

A further aspect of the present invention provides a method of producing maltose as an application of β-amylase derived from *Bacillus flexus*. In the production method according to the present invention, β-amylase derived from *Bacillus flexus* is allowed to act on a substrate consisting of polysaccharide or oligosaccharide having α-1,4 linkage of glucose as a main chain. Examples of the substrate may include soluble starch, potato starch, corn starch, amylopectin, glycogen, and maltooligosaccharide. The purity of the substrate is not particularly limited. Therefore, β-amylase may be allowed to act on the substrate in a state in which it is mixed with other materials. Furthermore, β-amylase may be allowed to act on two or more substrates simultaneously.

The production method of the present invention is characterized by using β-amylase derived from *Bacillus flexus*. Preferably, as the β-amylase, the above-mentioned β-amylase (the present enzyme) of the present invention is used.

The production method of the present invention is used for producing, for example, maltose-containing syrup, maltose starch syrup, and the like. The production method of the present invention may be used for improving the quality of bread or antioxidant means for rice-cake and rice-cake sweets.

EXAMPLE

Measurement Method of β-amylase Activity

The activity of β-amylase was measured as follows. To 0.5 ml of 0.1M phosphate-HCl buffer solution (pH 5.0) containing 1% soluble starch and 10 mM calcium acetate, 0.5 ml of enzyme solution was added. The mixture was incubated at 37° C. for 30 minutes. Then, 2.5 ml of DNS solution (0.2% DNS, 80 mM NaOH, 0.2 M potassium sodium tartrate tetrahydrate) was added to the mixture so as to stop the reaction. After the reaction was stopped, the reaction mixture was boiled for five minutes, the absorbance was measured at the wavelength of 530 nm. The enzyme amount when the absorbance measured at the wavelength of 530 nm is 1 is defined as one unit.

1. Confirmation of β-amylase Derived from *Bacillus flexus*

Four strains of *Bacillus flexus*, DSM1316, DSM1320, DSM1667, and APC9451 were cultured with shaking at 30° C. for three days by using a liquid medium containing the compositions shown in Table 1.

TABLE 1

| β-amylase production medium | |
| --- | --- |
| | (w/v) |
| Corn steep liquor | 2% |
| Soluble starch | 4% |
| Calcium carbonate | 2% |

The β-amylase activity in the resultant culture supernatant was measured by the above-mentioned measurement method of the β-amylase activity. The results are shown in Table 2.

TABLE 2

| | Activity |
| --- | --- |
| DSM1316 | 4.0 |
| DSM1320 | 14.8 |
| DSM1667 | 4.0 |
| APC9451 | 5.7 |

2. Production and Purification of β-amylase Derived from *Bacillus flexus* APC9451

*Bacillus flexus* APC9451 was cultured with shaking at 30° C. for three days by using a liquid medium having the compositions shown in Table 1. The obtained culture supernatant solution was four-times concentrated by using an UF membrane (AIP-0013, Asahi Kasei Corporation), and then ammonium sulfate was added thereto so as to obtain 60% saturation concentration. The precipitate fraction was dissolved again in 20 mM acetic acid buffer solution (pH 5.5). Then, to the mixture solution, ammonium sulfate was added so as to obtain 20% saturation concentration. The resultant precipitates were removed by centrifugation, and then subjected to HiPrep Butyl 16/10 FF column (GE Healthcare) that had been equilibrated with 20 mM acetic acid buffer solution (pH 5.5) containing ammonium sulfate with 20% saturation concentration. Then, adsorbed β-amylase protein was eluted by linear concentration gradient of ammonium sulfate from 20% saturation concentration to 0% saturation concentration.

The collected β-amylase activity fractions were concentrated by using an UF membrane, and then subjected to HiTrap CM FF column (GE Healthcare) that had been equilibrated with 20 mM acetic acid buffer solution (pH 5.5). The adsorbed β-amylase protein was eluted by linear concentration gradient of 0 M to 0.5 M of NaCl.

Furthermore, the collected β-amylase activity fractions were concentrated by using an UF membrane, and then subjected to HiLoad 16/60 Superdex200 column (GE Healthcare) that had been equilibrated with 20 mM acetic acid buffer solution (pH 5.5) containing 0.15 M NaCl, and eluted with the same buffer solution. The β-amylase activity fractions were collected and subjected to desalting and concentration by using ultrafiltration membrane, and thus purified enzyme preparation was obtained. The resultant purified enzyme was examined for the below mentioned properties. Furthermore, the enzyme was subjected to N-terminal amino acid sequence analysis and the internal peptide amino acid sequence analysis.

Figure 5:
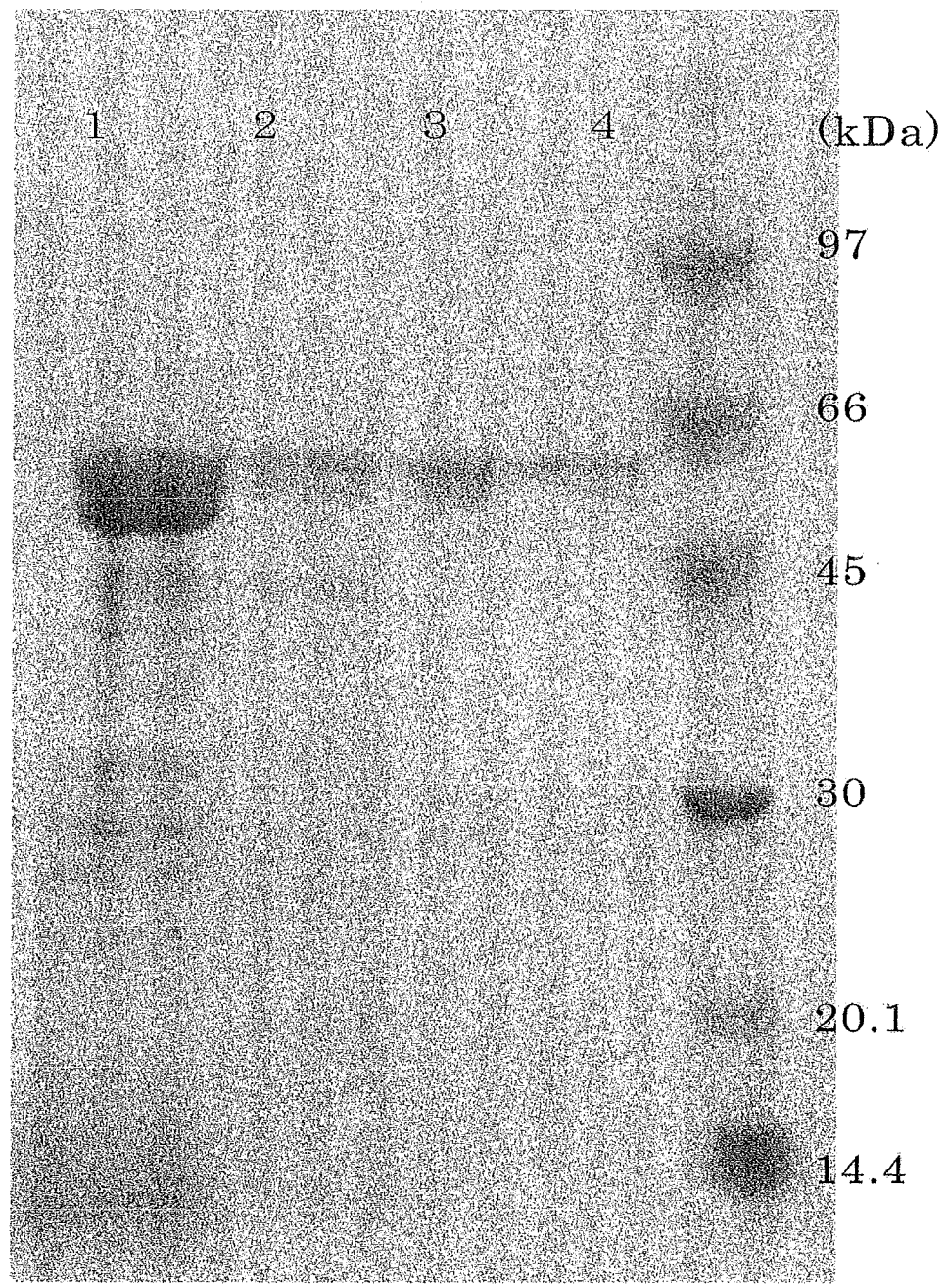
FIG. 5 shows the results of SDS-PAGE of purified β-amylase and samples during purification. Lane 1: ammonium sulfate fractionation, lane 2: HiPrepButyl 16/10 FF, lane 3: HiTrap CM FF, and lane 4: HiLoad 16/60 Superdex200

Note here that results of purification in each stage are shown in Table 3. The specific activity in the final stage was 2270 times as compared with that of the crude enzyme. FIG. 5 shows the results of SDS-PAGE (CBB staining) with 10-20% gradient gel of samples of each step in the purification process. It is shown that the purified enzyme preparation (lane 4) is a single protein in SDS-PAGE.

TABLE 3

| | Total protein amount (mg) | Total activity (U) | Specific activity (u/mg) | Collection rate (%) |
| --- | --- | --- | --- | --- |
| Concentrated solution | 27200 | 18700 | 0.69 | 100 |
| Ammonium sulfate fractionation | 2856 | 9054 | 3.17 | 48 |
| Butyl FF | 59.9 | 4120 | 68.8 | 22 |
| CM FF | 0.64 | 656 | 1031 | 4 |
| Superdex200 | 0.084 | 132 | 1569 | 1 |

3. Various Properties of Thermostable β-amylase (1) Optimum Reaction Temperature According to the above-mentioned β-amylase activity measurement method, reaction was carried out at the reaction temperatures of 25° C., 37° C., 50° C., 55° C., 60° C., 65° C., and 70° C. The values are shown as the relative activity when a value at a temperature exhibiting the maximum activity is defined as 100%. The optimum reaction temperature was around 55° C. (FIG. 1).

(2) Optimum Reaction pH

Figure 2:
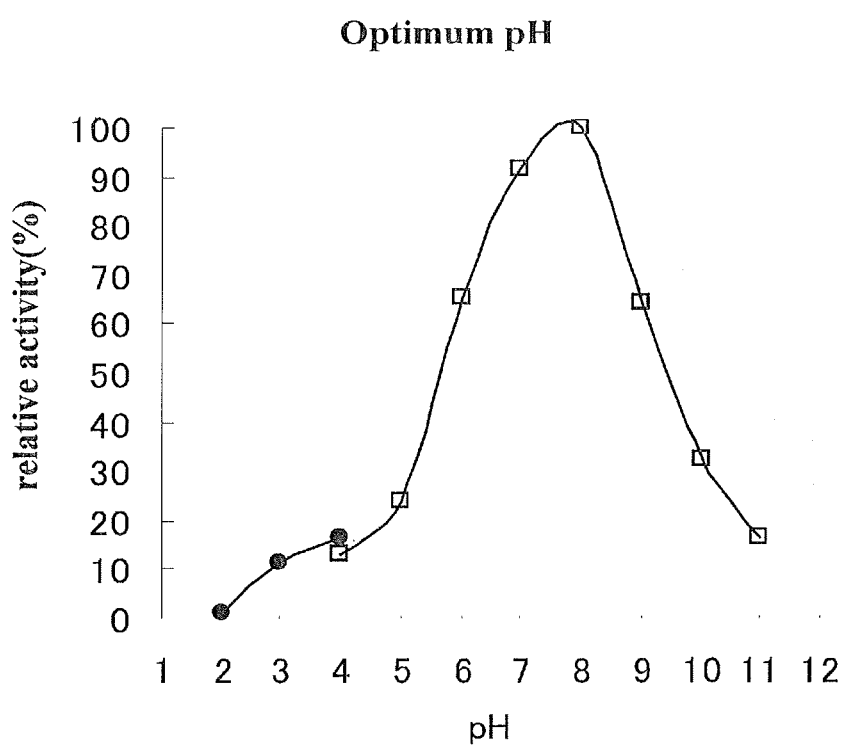
FIG. 2 is a graph showing an optimum pH of β-amylase derived from *Bacillus nexus*. ●: citric acid buffer at pH2, 3, and 4, □: Britton-Robinson buffer at pH4, 5, 6, 7, 8, 9, 10, and 11

For the substrate, 1% soluble starch was used, and the measurement was carried out in each buffer solution (citric acid buffer: pH2, pH3, and pH4, Britton-Robinson buffer: pH4, pH5, pH6, pH7, pH8, pH9, pH10, and pH11) at 37° C. for 10 minutes. The values are shown as the relative activity when pH exhibiting the maximum activity value is defined as 100%. The optimum reaction pH was about 8.0 (FIG. 2).

(3) Thermostability

Figure 3:
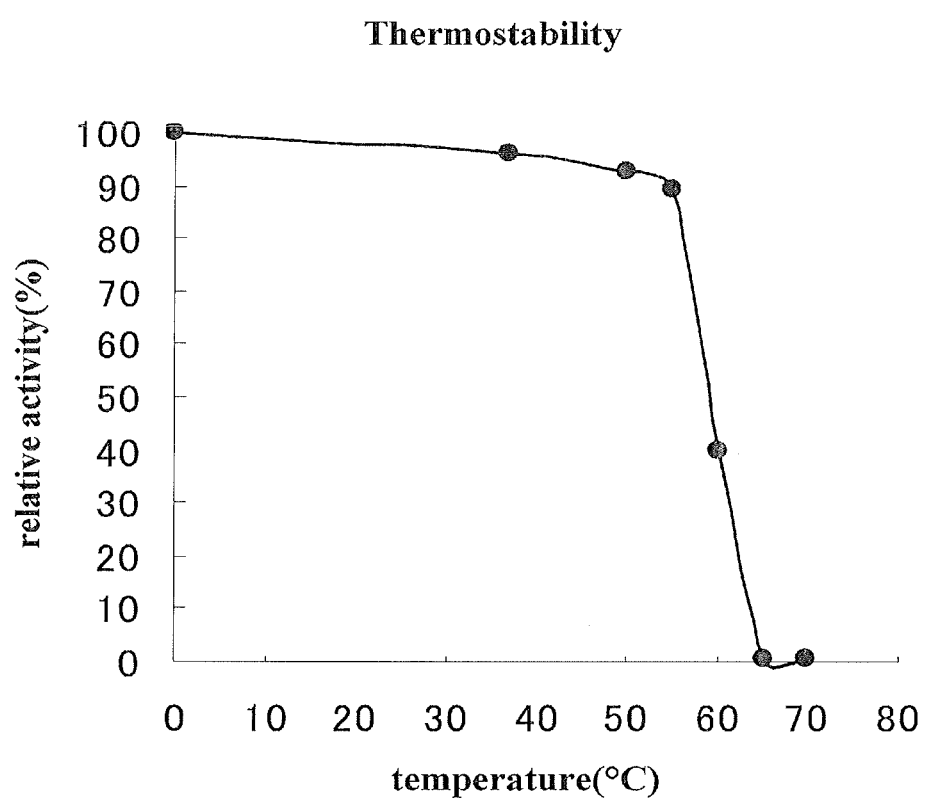
FIG. 3 is a graph showing thermostability of β-amylase derived from *Bacillus flexus*.

The enzyme solution (20 u/ml) was subjected to heat treatment in 0.1 M acetic acid—hydrochloric acid buffer solution (pH 5.0) containing 10 mM calcium acetate at each temperature of 37° C., 50° C., 55° C., 60° C., 65° C. and 70° C. for 10 minutes, and then the remaining activity was measured by the above-mentioned β-amylase activity measurement method. The values are shown as the remaining activity when the remaining activity with no heat treatment is defined as 100%. The heat treatment at 55° C. for 10 minutes shows the remaining activity of 90% or more. The thermostability was shows until 55° C. (FIG. 3).

Figure 4:
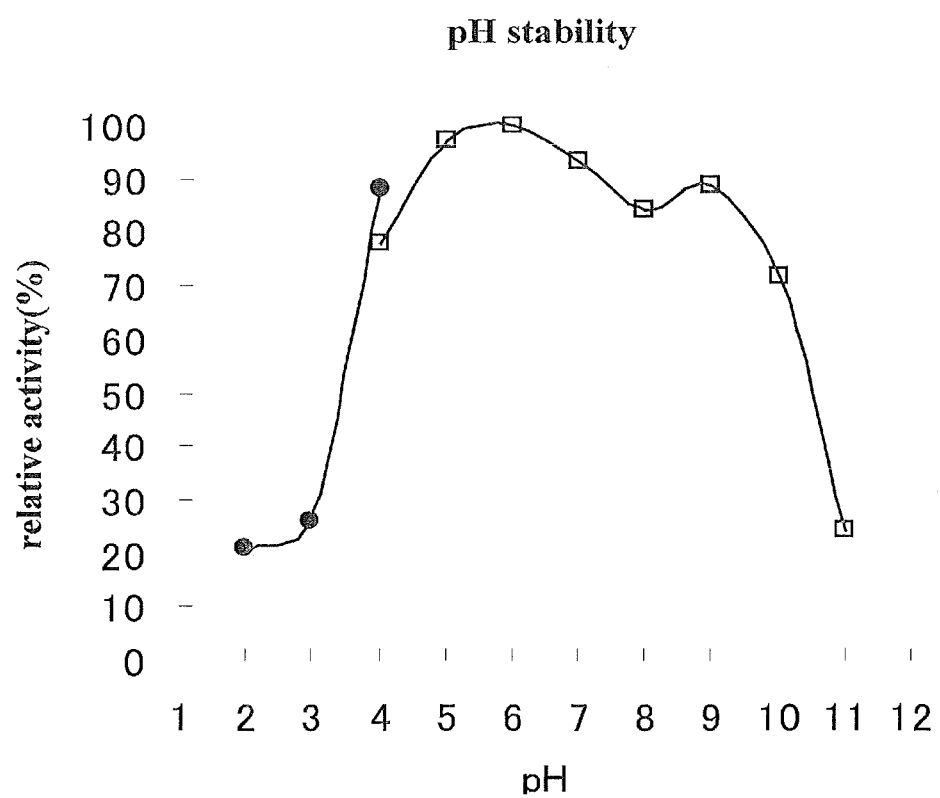
FIG. 4 is a graph showing pH stability of β-amylase derived from *Bacillus flexus*. ●: citric acid buffer at pH2, 3, and 4, □: Britton-Robinson buffer at pH4, 5, 6, 7, 8, 9, 10, and 11

(4) pH Stability

β-amylase was treated in each of the buffer solutions (citric acid buffer: pH2, pH3, and pH4, Britton-Robinson buffer: pH4, pH5, pH6, pH7, pH8, pH9, pH10, and pH11) at 30° C. for three house, and then the activity was measured by the above-mentioned β-amylase activity measurement method. The values are shown as the relative activity when pH exhibiting the maximum activity value is defined as 100%. The optimum reaction pH was 4 to 9 (FIG. 4).

(5) Molecular Weight Measurement by SDS-PAGE

SDS-PAGE was carried out according to the method by Laemmli et al. Note here that molecular weight marker used was Low Molecular Weight Calibration Kit for Electrophoresis (GE Healthcare), which included Phosphorylase b (97,000 Da), Albumin (66,000 Da), Ovalbumin (45,000 Da), Carbonic anhydrase (30,000 Da), Trypsin inhibitor (20,100 Da), and α-Lactalbumin (14,400 Da) as a reference protein. Electrophoresis was carried out at 20 mA/gel for 80 minutes by using a gradient gel (Wako) having a gel concentration of 10-20%, and the molecular weight was obtained. As a result, the molecular weight was about 60 kDa (FIG. 5).

(6) Isoelectric Point

When the isoelectric point of the present enzyme was measured by isoelectric point precipitation using Ampholine (electrification at 600V, at 4° C., for 48 hours), it was 9.7.

(7) Effect of Metal Ion and Inhibitor

To β-amylase in 0.1 M acetic acid—hydrochloric acid buffer solution (pH 5.0) containing 10 mM calcium acetate, 1 mM of various metal ions or inhibitor were added, respectively, treated at 30° C. for 30 minutes, and then the activity was measured by the above-mentioned β-amylase activity. The results are shown in Table 4. The values were shown as the relative activity when the metal ion and inhibitor were not added is defined as 100%. The activity was inhibited by Cu ion, iodine acetic acid, PCMB, and SDS.

TABLE 4

|  | Relative activity |
| --- | --- |
| $Na^+$ | 88 |
| $K^+$ | 96 |
| $Ca^{2+}$ | 130 |
| $Mn^{2+}$ | 222 |
| $Mg^{2+}$ | 103 |
| $Zn^{2+}$ | 96 |
| $Cu^{2+}$ | 46 |
| $Fe^{2+}$ | 105 |
| $Fe^{3+}$ | 113 |
| EDTA | 97 |
| N-ethylmaleimide | 93 |
| PCMB | 25 |
| monoiodoacetic acid | 14 |
| SDS | 37 |
| No additives | 100 |

(8) Substrate Specificity

The β-amylase activity with respect to each substrate was examined. The values are shown as the relative activity when the activity with respect to soluble starch is defined as 100%. As to oligosaccharides, the production amount of maltose was examined by the below-mentioned quantification amount of maltose. After 0.1 u/ml enzyme was reacted to 0.5% of each maltooligosaccharide at 37° C. for 30 minutes, quantification of maltose was carried out by HPLC (Aminex carbohydrate HPX-42A, BIO-RAD). A production amount of maltose when the substrate is soluble starch is defined as 100%, the relative activity with respect to each maltooligosaccharide was calculated from the production amount of maltose.

The results are shown in Table 5. The values were shown as the relative activity when a production amount of maltose with respect to soluble starch is defined as 100%. Cyclodextrin, pullulan, and dextran were almost broken down. Oligosaccharide did not act on maltotriose but well acted on the other oligosaccharides.

TABLE 5

| Substrate | Relative activity (%) |
| --- | --- |
| Maltotriose | 0 |
| Maltotetraose | 75 |
| Maltopentaose | 102 |
| Maltohexaose | 131 |
| Maltoheptaose | 111 |
| α-cyclodextrin | 0 |
| β-cyclodextrin | 1.4 |
| γ-cyclodextrin- | 0.6 |
| Amylose | 98 |
| Amylopectin | 83 |
| Pullulan | 3.4 |
| Dextran, | 1.9 |
| Glycogen | 51 |
| Potato starch | 78 |
| Corn starch | 85 |
| Waxy corn starch | 106 |
| Soluble starch | 100 |

4. Obtaining Gene Fragment Encoding β-amylase Derived from *Bacillus flexus*

(a) Isolation of Chromosome DNA

Genome DNA was prepared from a cell body of *Bacillus flexus* obtained in "1" by the Saito-Miura method (Biochim. Biophys. Acta, 72, 619-629, 1963).

(b) Determination of Partial Amino Acid Sequence

The purified preparation of β-amylase obtained in "1" was subjected to amino acid sequence analysis so as to determine the N-terminal amino acid sequence (SEQ ID NO: 1) and internal peptide amino acid sequence (SEQ ID NOs: 2 and 3) of 10 residues.

(c) Preparation of DNA Probe by PCR

Two types of mixed oligonucleotides were synthesized based on the N-terminal amino acid sequence and the internal amino acid sequence to obtain a PCR primer (SEQ ID NOs: 4 and 5). By using these primers and chromosome DNA of *Bacillus flexus* as a template, PCR reaction was carried out in the following conditions.

<PCR Reaction Solution>
  10×PCR reaction buffer solution (TaKaRa): 5.0 μl
  dNTP mixture solution (2.5 mM each, TaKaRa): 4.0 μl
  25 mM $MgCl_2$: 5 μl
  100 μM sense primer: 3.0 μl
  100 μM antisense primer: 3.0 μl
  Distilled water: 28.5 μl
  Chromosome DNA solution (140 μg/ml): 1 μl
  LA Taq DNA polymerase (TaKaRa): 0.5 μl
<PCR Reaction Conditions>
  Stage 1: denaturation (94° C., 5 minutes) 1 cycle
  Stage 2: denaturation (94° C., 30 seconds) 30 cycles
  Annealing (48° C., 30 seconds)
  Elongation (72° C., 1 minute)

About 0.86 kb of the obtained DNA fragment was cloned to pGEM-Teasy (Promega), and then the base sequence was confirmed. In immediately after the sense primer and immediately before the antisense primer, the base sequence encoding the above-mentioned partial amino acid sequence was found. This DNA fragment was defined as a DNA probe for full length gene cloning.

(d) Production of Gene Library

As a result of Southern hybridization analysis of chromosome DNA of *Bacillus flexus*, about 5.0 kb of single band that hybridizes to a probe DNA in KpnI decomposition product was confirmed. In order to clone this KpnI DNA fragment of about 5.0 kb, a gene library was produced as follows. Chromosome DNA prepared by the above-mentioned (a) was subjected to KpnI treatment. 28 µg of genome DNA of *Bacillus flexus*, 3 µl of 10×L buffer solution, 26 µl of distilled water, and 1 µl of KpnI were mixed and treated at 37° C. for 15 hours. The obtained decomposition product was ligated to pUC19 (TaKaRa) vector that had been subjected to KpnI treatment so as to obtain a gene library.

(e) Screening of Gene Library

The DNA fragment (0.86 kb) that had been obtained in the above-mentioned (c) was labeled with DIG-High Prime (Roche). This was used as a DNA probe, and then the gene library that had been obtained in (d) was subjected to screening by colony hybridization. A plasmid pUC19-BAF was obtained from the resultant positive colony.

(f) Determination of Base Sequence

The base sequence of the plasmid pUC19-BAF was determined according to a routine method. The base sequence (1638 bp) encoding β-amylase is shown in SEQ ID NO: 6. Furthermore, the amino acid sequence (545 amino acids) encoded by SEQ ID NO: 6 is shown in SEQ ID NO: 7. In this amino acid sequence, the amino acid sequence in the N-terminal region (SEQ ID NO: 1) and the internal amino acid sequences (SEQ ID NOs: 2 and 3), which had been determined in (b), were found.

5. Expression of β-amylase Derived from *Bacillus flexus* in *Escherichia coli*

(a) Structure of Expression Plasmid of β-amylase in *Escherichia coli*

Two types of oligonucleotides (SEQ ID NOs: 8 and 9) were synthesized based on the DNA sequence encoding the amino acid sequences in the N-terminal region and the C-terminal region, PCR primers were obtained. To the sense primer, the NdeI restriction enzyme recognition site was added, and to the antisense primer, the XhoI restriction enzyme recognition site was added. The PCR reaction was carried out in the following conditions by using these primers and a plasmid pUC19-BAF having a β-amylase gene as a template.

<PCR Reaction Solution>
  10×PCR reaction buffer solution (TOYOBO) 5.0 µl
  dNTP mixture solution (2.5 mM each, TOYOBO) 5.0 µl
  10 µM sense primer: 1.5 µl
  10 µM antisense primer: 1.5 µl
  25 mM MgSO₄ 2 µl
  Distilled water: 33 µl
  Plasmid pUC19-BAF solution (83 µg/ml): 1.0 µl
  KOD-Plus-DNA polymerase (TOYOBO): 1.0 µl
<PCR Reaction Conditions>
  Stage 1: denaturation (94° C., 2 minutes) 1 cycle
  Stage 2: denaturation (94° C., 15 seconds) 30 cycles
    Annealing (60° C., 30 seconds)
    Elongation (68° C., 2 minutes)

Figure 6:
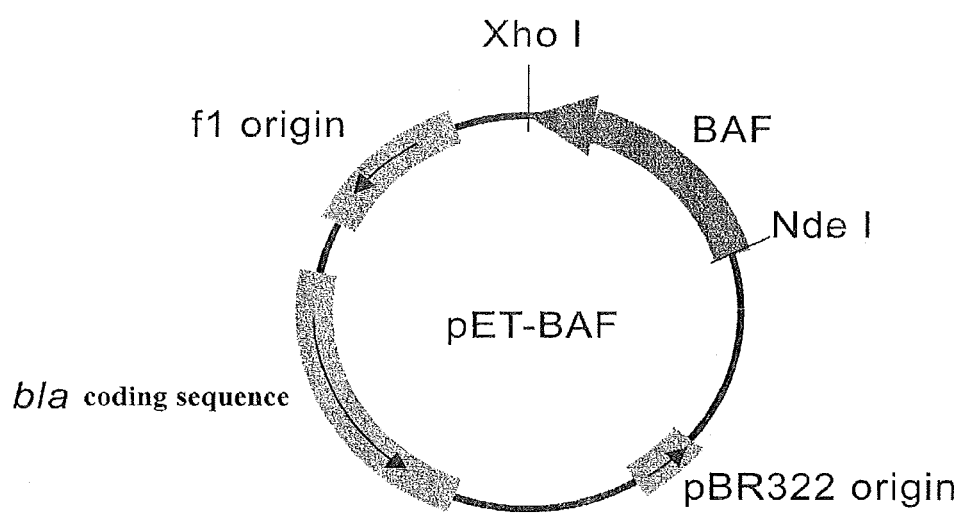
FIG. 6 shows a structure of an expression plasmid pET-BAF.

The obtained PCR product was confirmed by electrophoresis. Then, it was purified with GENE CLEANE III (34 µl), and 4 µl of 10×H buffer solution and 1 µl of NdeI and 1 µl of XhoI were added. The mixture was subjected to enzyme treatment at 37° C. for 15 hours. The restriction enzyme treatment solution was confirmed by electrophoresis and purified. Thereafter, the mixture was ligated to a vector pET20(b) (TAKARA BIO INC) that had been treated with NdeI and XhoI in advance, and thus the expression plasmid pET-BAF was obtained (FIG. 6). Furthermore, whether or not the base sequence encoding β-amylase in pET-BAF was correct was confirmed.

(b) Expression of β-amylase in *Escherichia coli*

The expression plasmid pET-BAF was introduced into *Escherichia coli* BL21 (DE3) (Novagen). From the transformants obtained as an ampicillin resistant strain, a strain holding pET-BAF in which the target β-amylase gene had been introduced by colony PCR was selected. Furthermore, a transformant of *Escherichia coli* BL21 (DE3) having an expression vector pET20(b) was obtained as a control. These transformants were cultured in 4 ml of LB medium containing 50 µg/ml ampicillin at 18° C., at 160 rpm for 47 hours, and cells were collected. The cell bodies were suspended in 0.5 ml of 20 mM acetic acid buffer solution (pH 5.5), to which 0.25 g of glass beads with 00.1 mm were added, the cell bodies were disrupted by using a multi-beads shocker (Yasui Kikai). As the disruption condition, 3.5 cycles of 30 seconds ON and 30 seconds OFF were repeated. The obtained cell free-extract was centrifuged to obtain a soluble components.

The activities of the obtained samples were measured according to the above-mentioned β-amylase activity measurement method. The results are shown in Table 6.

TABLE 6

|  | Activity (U/ml) | Protein (mg/ml) | Specific activity (U/mg) |
| --- | --- | --- | --- |
| pET-BAF | 43.5 | 7.9 | 5.5 |
| pET20(b) | 0.4 | 8.0 | 0.05 |

INDUSTRIAL APPLICABILITY

The β-amylase of the present invention has a thermostability that is comparable to the β-amylase derived from soybeans, and is suitable for applications that require the reaction at high temperatures. The use of the β-amylase of the present invention makes it possible to carry out the enzyme reaction at high temperatures that are less susceptible to contamination of various bacteria. Therefore, the β-amylase of the present invention is particularly useful in application such as food processing and saccharification.

The present invention is not limited to the description of the above embodiments and Examples. A variety of modifications, which are within the scopes of the following claims and which are easily achieved by a person skilled in the art, are included in the present invention.

Contents of the theses, Publication of Patent Applications, Patent Publications, and other published documents referred to in this specification are herein incorporated by reference in its entity.

The invention claimed is:

1. A recombinant vector containing a heterologous β-amylase DNA sequence selected from the group consisting of the following (A) to (C):
   (A) DNA encoding the amino acid sequence set forth in SEQ ID NO: 7;
   (B) DNA having a base sequence set forth in SEQ ID NO: 6; and
   (C) DNA having a base sequence that hybridizes to the complementary base sequence of the base sequence set forth in SEQ ID NO: 6 under the following stringent conditions: 50% formamide, 10×SSC (0.15 M NaCl, 15 mM sodium citrate, pH 7.0), 5×Denhardt solution, 1% SDS, 10% dextran sulfate, 10 µg/ml denatured salmon sperm DNA, and 50 mM phosphate buffer (pH 7.5) at 42° C. to 50° C. and washing with 0.1×SSC and 0.1% SDS at 65° C. to 70° C., and encoding a protein having a β-amylase activity.

2. A transformed and isolated host cell into which the β-amylase DNA sequence according to claim 1 is introduced.

3. A recombinant method of preparation of β-amylase, the method comprising the following steps (i) and (ii):
   (i) culturing the transformed and isolated host cell described in claim 2 under conditions in which a protein encoded by the DNA sequence is produced; and
   (ii) collecting the produced protein.

4. A method of making a transformed and isolated host cell according to claim 2 comprising the steps of:
   (A) making a recombinant vector containing the β-amylase DNA sequence selected from the group consisting of the following (i) to (ii):
      (i) DNA encoding the amino acid sequence set forth in SEQ ID NO: 7;
      (ii) DNA having a base sequence set forth in SEQ ID NO: 6;
      (iii) DNA having a base sequence that hybridizes to the complementary base sequence of the base sequence set forth in SEQ ID NO: 6 under the following stringent conditions: 50% formamide, 10×SSC (0.15 M NaCl, 15 mM sodium citrate, pH 7.0), 5×Denhardt solution, 1% SDS, 10% dextran sulfate 10 µg/ml denatured salmon sperm DNA, and 50 mM phosphate buffer (pH 7.5) at 42° C. to 50° C. and washing with 0.1×SSC and 0.1% SDS at 65° C. to 70° C., and encoding a protein having a β-amylase activity, and (B) inserting the vector of (A) into a transformed and isolated host cell.

\* \* \* \* \*

SEQUENCE LISTING

<160> NUMBER OF SEQ ID NOS: 9

<210> SEQ ID NO 1

```
<211> LENGTH: 10
<212> TYPE: PRT
<213> ORGANISM: Bacillus flexus

<400> SEQUENCE: 1

Ala Val Asn Gly Gln Ser Phe Asn Ser Asn
1               5                   10

<210> SEQ ID NO 2
<211> LENGTH: 7
<212> TYPE: PRT
<213> ORGANISM: Bacillus flexus

<400> SEQUENCE: 2

Leu Ala His Gln Ala Phe Asp
1               5

<210> SEQ ID NO 3
<211> LENGTH: 9
<212> TYPE: PRT
<213> ORGANISM: Bacillus flexus

<400> SEQUENCE: 3

Leu Ser Tyr Asn Ser Thr Tyr Gly Asp
1               5

<210> SEQ ID NO 4
<211> LENGTH: 23
<212> TYPE: DNA
<213> ORGANISM: Artificial Sequence
<220> FEATURE:
<223> OTHER INFORMATION: sense primer
<220> FEATURE:
<221> NAME/KEY: modified_base
<222> LOCATION: (3)..(3)
<223> OTHER INFORMATION: I
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (18)..(18)
<223> OTHER INFORMATION: n is a, c, g, or t

<400> SEQUENCE: 4
gcngtnaayg gncarwsntt yaa                                             23

<210> SEQ ID NO 5
<211> LENGTH: 21
<212> TYPE: DNA
<213> ORGANISM: Artificial Sequence
<220> FEATURE:
<223> OTHER INFORMATION: antisense primer
<220> FEATURE:
<221> NAME/KEY: misc_feature
<222> LOCATION: (7)..(7)
<223> OTHER INFORMATION: n is a, c, g, or t
<220> FEATURE:
<221> NAME/KEY: misc_feature
<222> LOCATION: (16)..(16)
<223> OTHER INFORMATION: n is a, c, g, or t
<220> FEATURE:
```

```
<221> NAME/KEY: misc_feature
<222> LOCATION: (19)..(19)
<223> OTHER INFORMATION: n is a, c, g, or t

<400> SEQUENCE: 5
rtcaarngcy tgrtgngcna r                                              21

<210> SEQ ID NO 6
<211> LENGTH: 1638
<212> TYPE: DNA
<213> ORGANISM: Bacillus flexus

<400> SEQUENCE: 6
atgtacaagc caattaaaaa gtttgcatca cttattgttt tgttaagttt tgttgccgct      60
ttcatattag gccaaccaa tagccaagca gcggtaaatg dacagtcgtt taactcgaat     120
tacaagacct atttaatggc accactaaag aaagtaacgg agtttactac gtgggaagct    180
tttgaaaatg accttcgaa ggcaaagcaa aatgggtttt acgctgtgac agtagatttt     240
tggtggggag atatggagaa aaacggtgac cagcagttcg acttttctta tgcacagcga    300
ttcgcacagg cagctcgaaa tgcgggaata aaaatggtgc cgattatctc gacgcatcaa    360
tgtggtggaa atgtaggaga tgactgtaac acgcctcttc cttcatggat ttggaatact    420
aaaacagatg atagcctata ttttaaatca gaaacaggta cagtaaacaa agaaacagta    480
aacccattag cgacagacgt aattacaaaa cagtacgggg agctatacac agcatttgcg    540
caagcgttag caccgtataa agacgttatt ccaaaggttt atttatcagg gggaccagct    600
ggtgagcttc gctatccttc atatacagct gctgatggga caggctaccc ttctagaggg    660
aaatttcaag catacacaga ctttgcaaaa tctaaattcc aaatgtgggc cgttaacaag    720
tatggctcgt tagcgggtgt aaaccaagca tggggactaa gttaacatc aacatcacaa     780 attttaccac cttcagatgg gaatcagttt ttaaaggatg gatataacac aaactatgga    840
aaagactttc tagaatggta tcaaggagtt ctgcaagacc atgcaaagcg tattggagca    900
ttagctcatc aagcctttga tccggtgttt aatgtgcctg taggagctaa aatagcaggg    960
atacactggc aatataataa tccaacaatg cctcatgctg ctgaaaagcc agcgggttat   1020
aataactaca gtacgttatt agactcattt aaaacagcca agctagattt gacgtttacg   1080
tgcttagaaa tggttgatag cgggacatat cctgagtatt caatgccaaa aacgttagta   1140
aaagaagttg caagcctagc aaacgcaaaa gggattgtat aaatggtga aaatgcttta    1200 agtatcggaa gtgaagagca gtataaacgc gcagctgaaa tgacatttaa ctataacttt   1260
gcgggcttta cgcttttaag attctatgat gttattaata actcaacgcg tatgagccag   1320
tttaatcagc acttaaatat aaaaccggtt gcacagacaa tggttgttaa aaatgcacct   1380
acatcgtctg gagagagtgt ttacatcgtc ggagatcgtc ctgaacttgg acagtgggac   1440
acaatcgctt atccaattaa actctcttac aactcaacgt acggagattg gagaggaacc   1500
gttaatttcc cagccgatcg aagcgttcag ttcaaagcga ttatcaagcg ctcggatggc   1560
tcattaaaat catggcaacc aacccagcag tattggaatg ttccaggaac gcctacaacg   1620
tatacgaata attggtaa                                                  1638

<210> SEQ ID NO 7
<211> LENGTH: 545
<212> TYPE: PRT
<213> ORGANISM: Bacillus flexus

<400> SEQUENCE: 7
```

```
Met Tyr Lys Pro Ile Lys Lys Phe Ala Ser Leu Ile Val Leu Leu Ser
1               5                   10                  15

Phe Val Ala Ala Phe Ile Leu Gly Pro Thr Asn Ser Gln Ala Ala Val
            20                  25                  30

Asn Gly Gln Ser Phe Asn Ser Asn Tyr Lys Thr Tyr Leu Met Ala Pro
            35                  40                  45

Leu Lys Lys Val Thr Glu Phe Thr Thr Trp Glu Ala Phe Glu Asn Asp
50                  55                  60

Leu Arg Lys Ala Lys Gln Asn Gly Phe Tyr Ala Val Thr Val Asp Phe
65                  70                  75                  80

Trp Trp Gly Asp Met Glu Lys Asn Gly Asp Gln Phe Asp Phe Ser
                85                  90                  95

Tyr Ala Gln Arg Phe Ala Gln Ala Ala Arg Asn Ala Gly Ile Lys Met
                100                 105                 110

Val Pro Ile Ile Ser Thr His Gln Cys Gly Gly Asn Val Gly Asp Asp
            115                 120                 125

Cys Asn Thr Pro Leu Pro Ser Trp Ile Trp Asn Thr Lys Thr Asp Asp
130                 135                 140

Ser Leu Tyr Phe Lys Ser Glu Thr Gly Thr Val Asn Lys Glu Thr Val
145                 150                 155                 160

Asn Pro Leu Ala Thr Asp Val Ile Thr Lys Gln Tyr Gly Glu Leu Tyr
                165                 170                 175

Thr Ala Phe Ala Gln Ala Leu Ala Pro Tyr Lys Asp Val Ile Pro Lys
                180                 185                 190

Val Tyr Leu Ser Gly Gly Pro Ala Gly Glu Leu Arg Tyr Pro Ser Tyr
                195                 200                 205

Thr Ala Ala Asp Gly Thr Gly Tyr Pro Ser Arg Gly Lys Phe Gln Ala
                210                 215                 220

Tyr Thr Asp Phe Ala Lys Ser Lys Phe Gln Met Trp Ala Val Asn Lys
225                 230                 235                 240

Tyr Gly Ser Leu Ala Gly Val Asn Gln Ala Trp Gly Leu Ser Leu Thr
                245                 250                 255

Ser Thr Ser Gln Ile Leu Pro Pro Ser Asp Gly Asn Gln Phe Leu Lys
                260                 265                 270

Asp Gly Tyr Asn Thr Asn Tyr Gly Lys Asp Phe Leu Glu Trp Tyr Gln
                275                 280                 285

Gly Val Leu Gln Asp His Ala Lys Arg Ile Gly Ala Leu Ala His Gln
                290                 295                 300

Ala Phe Asp Pro Val Phe Asn Val Pro Val Gly Ala Lys Ile Ala Gly
305                 310                 315                 320

Ile His Trp Gln Tyr Asn Asn Pro Thr Met Pro His Ala Ala Glu Lys
                325                 330                 335

Pro Ala Gly Tyr Asn Asn Tyr Ser Thr Leu Leu Asp Ser Phe Lys Thr
                340                 345                 350

Ala Lys Leu Asp Leu Thr Phe Thr Cys Leu Glu Met Val Asp Ser Gly
            355                 360                 365

Thr Tyr Pro Glu Tyr Ser Met Pro Lys Thr Leu Val Lys Glu Val Ala
            370                 375                 380

Ser Leu Ala Asn Ala Lys Gly Ile Val Leu Asn Gly Glu Asn Ala Leu
385                 390                 395                 400

Ser Ile Gly Ser Glu Glu Gln Tyr Lys Arg Ala Ala Glu Met Thr Phe
                405                 410                 415
```

```
Asn Tyr Asn Phe Ala Gly Phe Thr Leu Leu Arg Phe Tyr Asp Val Ile
            420                 425                 430

Asn Asn Ser Thr Arg Met Ser Gln Phe Asn Gln His Leu Asn Ile Lys
        435                 440                 445

Pro Val Ala Gln Thr Met Val Val Lys Asn Ala Pro Thr Ser Ser Gly
    450                 455                 460

Glu Ser Val Tyr Ile Val Gly Asp Arg Pro Glu Leu Gly Gln Trp Asp
465                 470                 475                 480

Thr Ile Ala Tyr Pro Ile Lys Leu Ser Tyr Asn Ser Thr Tyr Gly Asp
                485                 490                 495

Trp Arg Gly Thr Val Asn Phe Pro Ala Asp Arg Ser Val Gln Phe Lys
            500                 505                 510

Ala Ile Ile Lys Arg Ser Asp Gly Ser Leu Lys Ser Trp Gln Pro Thr
        515                 520                 525

Gln Gln Tyr Trp Asn Val Pro Gly Thr Pro Thr Thr Tyr Thr Asn Asn
    530                 535                 540

Trp
545

<210> SEQ ID NO 8
<211> LENGTH: 29
<212> TYPE: DNA
<213> ORGANISM: Artificial Sequence
<220> FEATURE:
<223> OTHER INFORMATION: sense primer

<400> SEQUENCE: 8
gtactcatat ggcggtaaat ggacagtcg                                    29

<210> SEQ ID NO 9
<211> LENGTH: 29
<212> TYPE: DNA
<213> ORGANISM: Artificial Sequence
<220> FEATURE:
<223> OTHER INFORMATION: antisense primer

<400> SEQUENCE: 9
cgactctcga gttaccaatt attcgtata                                    29
```